(12) United States Patent
Nakajima et al.

(10) Patent No.: US 7,368,026 B2
(45) Date of Patent: May 6, 2008

(54) BIOCHEMICAL ANALYSIS UNIT AND METHOD FOR PRODUCING THEREOF

(75) Inventors: Kenji Nakajima, Kanagawa (JP); Akifumi Kato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 734 days.

(21) Appl. No.: 10/355,257

(22) Filed: Jan. 31, 2003

(65) Prior Publication Data

US 2003/0153070 A1     Aug. 14, 2003

(30) Foreign Application Priority Data

Jan. 31, 2002    (JP)  ............................. 2002-024234

(51) Int. Cl.
    *B32B 37/00*     (2006.01)
(52) U.S. Cl. .................. 156/199; 156/261; 156/293
(58) Field of Classification Search ............... 156/250, 156/256, 261, 269, 555, 580, 582, 583.1, 156/196, 199, 293
See application file for complete search history.

(56) References Cited

U.S. PATENT DOCUMENTS

| | | | |
|---|---|---|---|
| 4,416,719 A * | 11/1983 | Horiuchi | 156/359 |
| 4,493,815 A * | 1/1985 | Fernwood et al. | 422/101 |
| 5,380,644 A | 1/1995 | Yonkoski et al. | |
| 5,394,498 A | 2/1995 | Hinterlong et al. | |
| 5,807,522 A | 9/1998 | Brown et al. | |

2001/0026917 A1    10/2001    Neriishi et al.

FOREIGN PATENT DOCUMENTS

| | | |
|---|---|---|
| EP | 1 267 169 A2 | 12/2002 |
| JP | 58-069281 | 4/1983 |
| JP | 59-056479 | 3/1984 |
| JP | 59-75200 | 4/1984 |
| JP | 59-083057 | 5/1984 |
| JP | 60-010174 | 1/1985 |
| JP | 60-066998 | 4/1985 |
| JP | 60-101179 | 6/1985 |
| JP | 62-170950 | 7/1987 |
| JP | 63-188135 | 8/1988 |
| JP | 02-276997 | 11/1990 |
| JP | 06-301140 | 10/1994 |

OTHER PUBLICATIONS

Japanese Abstract No. 11052187, dated Feb. 26, 1999.

* cited by examiner

*Primary Examiner*—James Sells
(74) *Attorney, Agent, or Firm*—Sughrue Mion, PLLC

(57) ABSTRACT

In producing a biochemical analysis unit (1), an adhesive agent (25) is applied to a base. After calcinations, the adhesive agent (25) forms an adhesive layer (25a, 25b) on a wall of each holes (3) formed in the base (2). Thereafter, an excess adhesive agent (25c) remaining on the surface of the base (2) is removed. Then, a sheet of an absorptive material (4) is set to overlap the base (2). A press roller pair (27, 28) presses them to charge the absorptive material (4) in the holes (3). Thus the absorptive material (4) is fixed in the hole (3) of the base (2) through the adhesive layer (25a, 25b).

11 Claims, 8 Drawing Sheets

BIOCHEMICAL ANALYSIS UNIT AND METHOD FOR PRODUCING THEREOF

BACKGROUND OF THE INVENTION

1. Field of the Invention

The present invention relates to a biochemical analysis unit and a method for producing thereof, and particularly to a biochemical analysis unit and a method for producing thereof which prevents to cause a noise when a labeling substance or a fluorescent substance radiates or emits light.

2. Description Related to the Prior Art

As disclosed in Japanese Patent Publications No. 1-60784, 1-60782, and 4-3952, an auto radiography image analyzing system is known for detecting a radioactive labeling substance which are dosed with a living organism. In the auto radiography image analyzing system, a part of the living organism on dosage of the labeling substance is used as a sample. When the sample overlaps disposed for a predetermined time on a stimulable phosphor sheet having a stimulating phosphor layer, the energy of radiation irradiated from the radioactive labeling substances is accumulated and recorded in the stimulable phosphor layer. Thereafter when the stimulable phosphor layer is scanned in an electromagnetic wave, the stimulable phosphor is excited, and a stimulation light emitted from the stimulable phosphor layer is photoelectrically detected. Thus a detection data is obtained and effected in image processing for forming an image on a display, such as a CRT or the like, or a recording material.

In the auto radiography image analyzing system, a development processing is not necessary. Further the image data obtained from the detection data can be processed to reproduce a desired image and therefore a quantity analysis becomes possible with a computer.

Further, recently, an analyzing system is known for analyzing a substances derived from living organism, for example, a nucleic acid (such as DNA and RNA), proteins and the like. In the analyzing system, the substance derived from living organism that is labeled with a labeling substance is set in the electromagnetic waves for exiting the labeling substance. Thus the excited light is generated and detected such that the detecting data is obtained to form the image.

As the analyzing system, there are a fluorescent analyzing system, a chemiluminescence analyzing system and the like.

In the fluorescent analyzing system is carried out the determination of genetic sequence, expression level of gene, routs of metabolism, absorbance and discharge, the separation or the identification of protein, the estimation of molecular weight or properties of protein, or the like. The substance derived from living organism, such as protein, is labeled with the fluorescent substances by dipping a gel support in a solution containing a fluorescent substance after the support on which a plurality of proteins are distributed by means of electrophoresis. When the sample is excited with the exciting light, then a fluorescent light generated from the fluorescent substance is detected to form an image. Thus positions and amount distributions of proteins on the gel support can be known. The fluorescent analyzing system has a merit in that the radioactive substance is not used, and that the genetic sequence and the like are easily determined.

In the fluorescent analyzing system, a western blotting method and a southern blotting method may be used. In the western blotting method, a part of proteins after electrophoresis is transferred to a solid base such as nitrocellulose sheet from the gel support. Then, an antibody which makes a selective reaction with the substance of living organism to be detected is labeled with the labeling substance such as fluorochrome to produce a probe. When the probe and the protein are combined, the protein is selectively labeled. The positions or the quantitative distribution of protein on the solid base can be detected by sensing a fluorescent light from the fluorochrome which is excited with exciting light. The western blotting method is also used for searching a distribution of DNA in a DNA segment.

In the southern blotting, after a plurality of DNA fragments on a gel support is distributed by means of electrophoresis and denaturated, at least a part of DNA fragments is transferred onto a transfer support such as nitrocellulose support. The denaturated DNA fragments are hybridized with a probe in which a fluorescent dye labels DNA or RNA complementary to the denaturated DNA fragments. In the hybridization, only the target DNA fragments are selectively labeled. When the fluorescent dye is excited, then the distribution of the target DNA on the transfer support is detected. Further, it is preferable to use the enzyme. In this case, the comprementary DNA is combined with the enzyme, and contacted to the fluorescent substrate, and the fluorescent substrate is transformed to the fluorescent substance. Then the fluorescent light irradiated from the fluorescent substance is sensed to detect the distribution of the target DNA.

In the chemiluminescent analyzing system, the labeling substance is used, which generates a visible chemiluminescent light by contacting to the chemiluminescent substrate. The substance fixed on a support is selectively labeled with the labeling substance, and thereafter contacted to the chemiluminescent substrate to emit the chemiluminescent light which is photometry detected.

Recently, there is known a micro array analyzing system. In the micro array analyzing system, a specific binding substance is used, which can be bound with the substance derived from living organism, such as hormone, tumor marker, enzyme, antibody, antigen, abzyme, other protein, nucleic acid, cDNA, DNA, RNA or the like. According to the specific binding substance are established sequence, base length, composition and the like.

In the micro array analyzing system, the several substances labeled with a labeling substance are spotted at different positions on a surface (glass plate, porous membrane and the like) of the biochemical analysis unit. The substances are combined with the specific binding substance previously spotted by a spotting device, and labeled with the labeling substance or the luminescent substance for producing the micro array. When the exciting light is irradiated, a light (such as luminescence) is generated by a labeling substance in the micro array and photoelectrically detected.

Further, an improvement of the micro array is used with the radioactive labeling substance for labeling the substance of living organism that is bounded with the specific binding substance. The micro array is superposed on the stimulable phosphor sheet to make an exposure of the stimulating phosphor layer. Then the exciting light is impinged on the stimulating phosphor layer, and the stimulation light emitted from the stimulating phosphor layer is photoelectrically detected.

According to the micro array image analyzing system, several sorts of the specific biding substance are formed as spots in high density. After labeled with the labeling substance, the substance derived from living organism is dropped on the spots to hybridize with the specific binding substance. Thus the analysis of the substance derived from the living organism is made in a short time.

In the above mentioned image analyzing system is used a biochemical analysis unit in which a micro array is formed on a support, such as a glass plate, a membrane or the like. The micro array has plural spots for detecting plural kinds of materials. However, in the biochemical analysis unit as the electromagnetic wave or the light generated from the labeling substance in the neighboring spots is mixed, noises are caused in the detection data. In this case, if the radioactive labeling substance is used, for example, the quantitative analysis of the substance derived from living organism is not made correctly. Especially, if the labeling substance is spotted in high density, the quantitative analysis becomes simply bad.

SUMMARY OF THE INVENTION

An object of the present invention is to provide a biochemical analysis unit and a method of producing thereof which prevents the generation of a noise and with which a biochemical analysis is carried out in high resolution.

Another object of the present invention is to provide a biochemical analysis unit and a method for producing thereof in which a porous material charged in holes of a base is prevented from peeling.

In order to achieve the object and the other objects, an adhesive agent is applied to a substrate of a biochemical analysis unit of the present invention. An absorptive material fixedly fills in each hole formed in the substrate. A grass transition temperature of the adhesive agent is more than −20° C. and less than 50° C. Preferably the adhesive agent is styrene butadiene rubber or acrylonitril butadiene rubber.

In a preferred embodiment of the present invention, a surface of a substrate is coated with an adhesive agent, and thereafter, an excess adhesive agent is removed such that the adhesive agent remains in holes formed in the substrate. Then the substrate is heated to solidify the adhesive agent, and another excess adhesive agent with which holes are totally or partially covered is removed, which is made with laser ablation, punch, or heating the substrate so as to soften the adhesive agent. In another preferred embodiment, an absorptive material is in contact with the substrate, and pressed with a press member into the plural holes in which the adhesive agent is applied, so as to be charged in the holes and so as to be adhere to the holes. Thereafter, another absorptive material remaining on the substrate is removed. Thus, in the substrate, the absorptive material is charged only in the holes.

According to the invention, as the adhesive agent is applied to the wall of the hole, the absorptive material is hardly peeled from the holes.

BRIEF DESCRIPTION OF THE DRAWINGS

The above objects and advantages of the present invention will become easily understood by one of ordinary skill in the art when the following detailed description would be read in connection with the accompanying drawings.

PREFERRED EMBODIMENTS OF THE INVENTION

Figure 1:
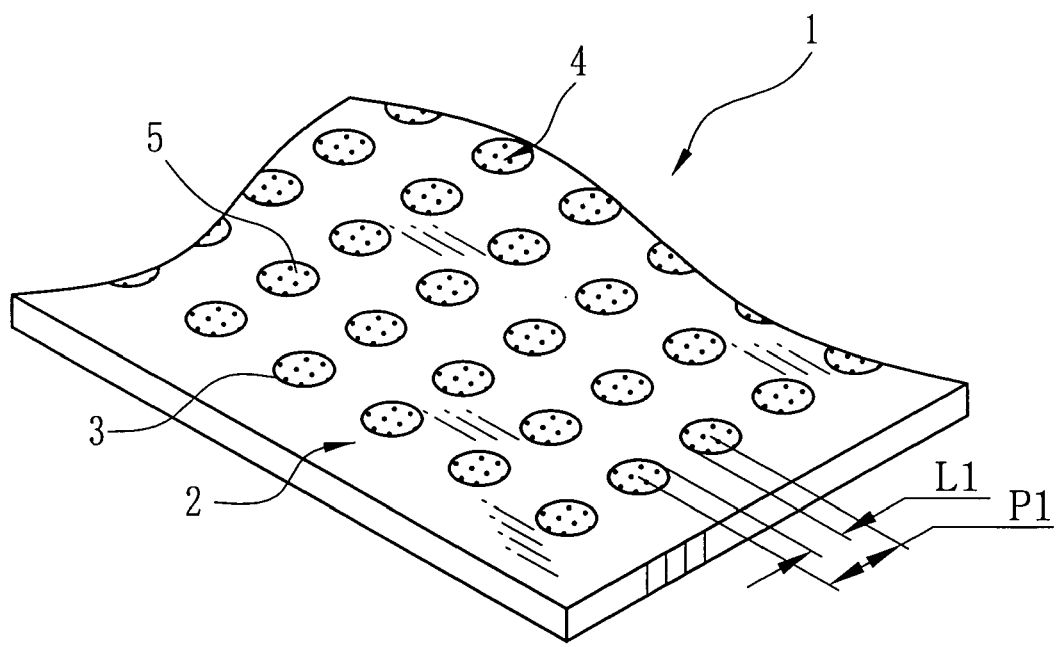
FIG. 1 is a perspective partial view of a biochemical analysis unit of the present invention.

In FIG. 1, a biochemical analysis unit 1 has a substrate 2 provided with plural holes 3 and a porous material 4. The porous material 4 is used as an absorptive material, which is charged in the holes 3. In the hole 3, a spot region 5 is formed. On the spot region 5 is spotted a specific binding substance whose structure and characteristic are known. Thereafter the specific binding substance is processed and fixed in the porous material 4 in the spot region 5.

When the biochemical analysis unit 1 is used for the clinical examination, a substance derived from living organism is dropped on each of the spot regions 5 constructing a micro array. The specific biding substances are hybridized with a substance derived from living organism that is labeled with a labeling substance. As the specific binding substance, there are radioactive substance, luminescent substance, and chemniluminescent substance. Then after predetermined processing, a radioactive ray or a light is emitted from the labeling substance in the spot region 5 in each hole 3.

The substrate 2 is formed by cutting a continuous substrate 200 (see FIG. 6) to have a predetermined size. Further, as the substrate 2, following materials are used, metal, ceramic, and the like, through which none of the radioactive ray or a light passes, or which decrease the amount of the radioactive ray or the light. Further, the substrate 2 can be made of a plastic in which the holes 3 are easily formed. In this case, however, particles of metal or ceramic are provided in the plastic in order to decreases the amount of the radioactive ray or the light.

As the metal material for forming the substrate 2, there are, for example, copper, silver, gold, zinc, lead, aluminum, titanium, tin, nickel, cobalt, tantalum, or alloys, such as stainless, brass and the like.

As the plastic material, there are, for example, polyolefin (polyethylene, polypropylene and the like), acryl resin (polystyrene, polymethylmethacrilate and the like), polyesters (polyvinyl chloride, polyvinylidene chloride, polyvinylidene fluoride, polytetrafluoro ethylene, polychlorotrifluoro ethylene, polycarbonate, polyethylene naphthalate, polyethylene terephthalate and the like), fatty acid polyamide (nylon-6, nylon-66 and the like), silicon resin (polyimide, polysulfone, polyphenylene sulfide, polydiphenyl siloxane and the like), phenol resin (noborac and the like), epoxy resin, cellulose acetate, cellulose (polyurethane, cellulose acetate, nitrocellulose and the like), copolymer (butadiene-styrene copolymer). A blend of these plastics may be also used.

As the particles contained in the plastics, there are metallic particles and a glass fiber. As the metallic particles, there are silicone dioxide, alumina, titanium dioxide, iron oxide, copper oxide and the like.

As the ceramics material, there are alumina, zirconia, magnesia, quartz and the like. It is noted that the sorts of the above materials are not restricted in them.

In the biochemical analysis unit 1, the radioactive ray or the light emitted from the spot region 5, when arriving at the neighboring spot region through the substrate 2, is decreased less than ⅕ and preferably ⅒.

A transmission distance of the electric ray is in inverse proportion to the density of material in which the electric ray passes. Accordingly, when the labeling substance is a widely used radioisotope, such as $^{32}P$, $^{33}P$, $^{35}S$, $^{14}C$ and the like, the averaged density of the substrate 2 is more than 0.6 g/cm$^3$, preferably 1-20 g/cm$^3$, and especially 2-10 g/cm$^3$. In this case, the substrate 2 shields the radioactive ray emitted from the radioisotope in each spot region 5. Therefore the generation of noise in the detection data, which is caused from the scattering and transmission of the radioactive ray, is prevented.

The thickness of the substrate 2 is 50-1000 μm, preferably 100-500 μm.

It is preferable that the holes 3 are formed at high density. Accordingly, the size of each hole 3 is less than 5 mm$^2$, preferably less than 1 mm$^2$, particularly 0.3 mm$^2$, and especially more than 0.001 mm$^2$.

A pitch P1 of the holes 3 that is defined as a distance between centers of neighboring holes is determined to 0.05-3 mm. An interval L1 defined as a distance between edges of the neighboring holes 3 is determined to 0.01-1.5 mm. The density of number of the holes is determined to more than 10/cm$^2$, preferably more than 100/cm$^2$, particularly more than 500/cm$^2$, and especially 1000/cm$^2$. However, there is an upper limit. Namely, the density is preferable less than 100,000/cm$^2$, and especially 10,000/cm$^2$.

Note that the holes 3 may not be formed at a same pitch when the above conditions are filled. For example, the holes 3 in alignment in one direction may be alternately arranged in another direction perpendicular to the one direction. Further the holes 3 may be randomly formed. The holes 3 may be formed to have triangle, tetragonal, hexagonal, other polygonal, elliptic and other forms. Furthermore, the absorptive spot region 5 of the rectangular form which is very long in a longitudinal direction thereof may be formed in a stripe manner.

Figure 2A:
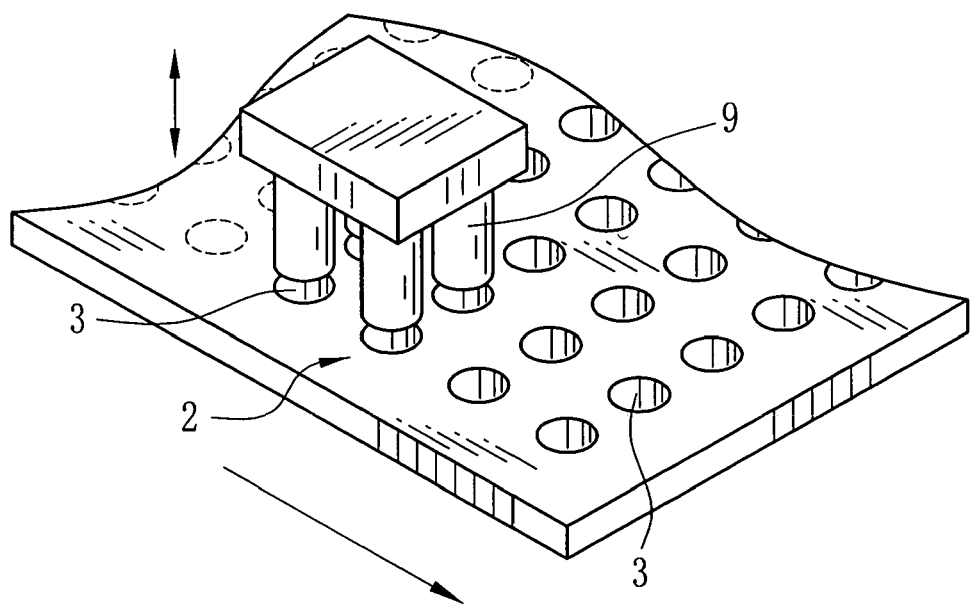
FIG. 2A is a perspective partial view of a substrate of the biochemical analysis unit, illustrating a situation that holes are formed with punch.

As shown in FIG. 2A, the holes 3 are formed with punches 9. Further, the holes 3 may be formed with discharging electrodes which are arranged at the pitch P1. In this case, the substrate 2 is grounded and supplied in insulating fluid, such as oil, air, and the like, and thereafter the discharging electrodes are closed to the substrate 2. When a high voltage is supplied to the electrodes, an electric discharge causes to heat the substrate 2, whose parts confronting to the electrodes are evaporated to form the holes 3.

Figure 2B:
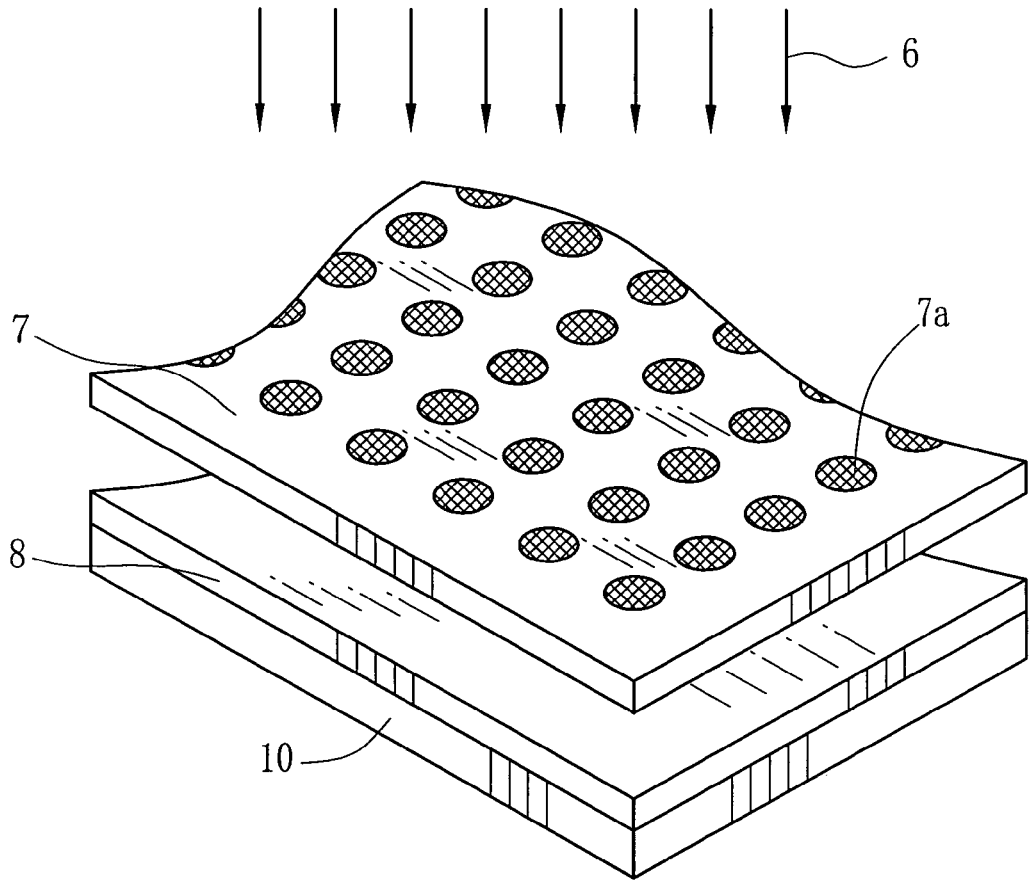
FIG. 2B is a perspective partial view illustrating a method for forming the substrate in photo etching method.
Figure 3:
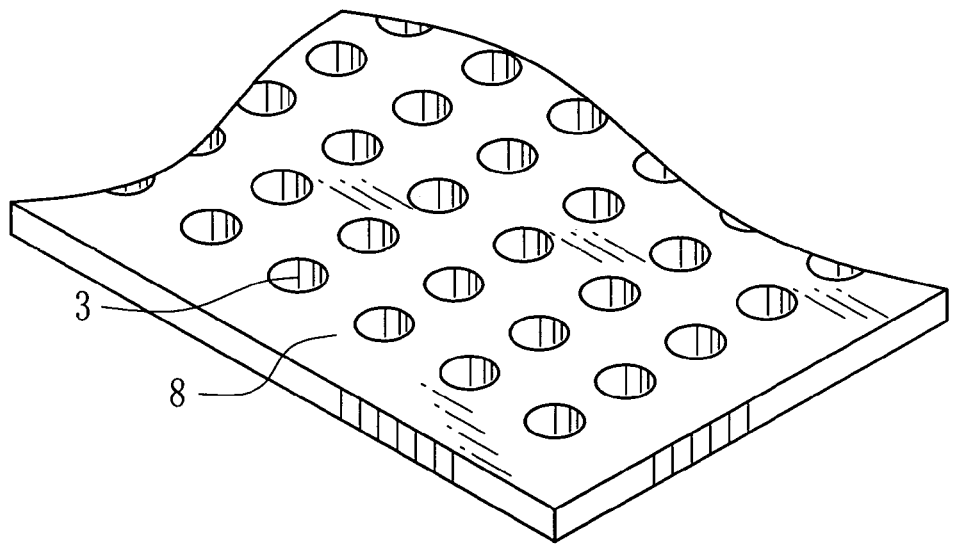
FIG. 3 is a perspective view of the substrate which is made with the photo etching method in FIG. 2B.

The holes 3 in the substrate 2 may be formed in making a photolithograph and etching. As shown in FIG. 2B, on a support 10, there is a coating layer 8 formed by applying a light or ultraviolet ray curing agent. On the coating layer 8, a mask 7 having hole patterns 7a is piled. Then a light is illuminated through the mask 7 to the coating layer 8 to make the photolithograph. Thus part of the coating layer 8 around the hole patterns 7a is hardened. Thereafter, the coating layer 8 is inserted in an organic solvent to solve the other parts of the coating layer 8 that is not hardened. Thereafter the coating layer 8 are removed from the support 10 to become the substrate in FIG. 3. Note that the support 10 is preferably formed of polyethylene, polypropylene, polyethylene terephthalate, polytetrafluoroethylene and the like.

It is preferable to use ultraviolet curable compounds as the coating layer 8. The ultraviolet curable compounds are produced from an optical polymerizer and an ultraviolet curable resin material. The optical polymerizer is, for example, hydrogen pulling type initiator (benzophenone initiator), radical fragmentation type initiator (acetophenone initiator, triazine initiator). Further, the ultraviolet curable resin material is acrylic acid esters (acrylic acid ethyl, acrylic acid butyl, acrylic acid 2-ethylhexil), methacrylic acid esters (methacrylic acid methyl, methacrylic acid ethyl, methacrylic acid butyl, ethylene glycol dimethacrylate), ester of high carbon alcohol and (metha-)acrylic acid (ethylene glycol di(meta)acrylate, 1,4-diclohexane-diacrylate, pentaerythritol tetra(meta)acrylate), dipentaerythritol tri(meta)acrylate, trimethylolpropane tri(meta)acrylate, trimethylolethane tri(meta)acrylate, dipentaerythritol tetra(meta)areylate, dipentaerythritol penta(meta)acrylate, pentaerythrytol hexa(meta)acrylate), 1,2,3-cyclohexane tetramethacrylate, polyurethane polyacrylate, polyester polyacrylate) and the like. These materials may be mixed to use.

As organic solvents used for etching there are ketones such as acetone, methylethylketone. However other solvents may be used if possible to solve the ultraviolet curing compounds. It is preferable that the support 10 is affected in a supersonic wave in the etching liquid when etching is carried out.

When the substrate 2 is made of metal, the holes 3 are formed with electrolytic etching. A resist is applied on the metallic substrate 2, and an exposure is made with a photomask pattern. For example, a metal plate and a platinum are used as an anode and a cathode, and set into solutions of strong acids, such as sulfuric acid, fluoric acid, phosphoric acid and the like. Then after forming the holes 3, the resist on the metallic substrate 2 is removed.

Further, high power laser beam may be emitted to form the plural holes on the substrate 2. In this case, when the laser beam is scanned on the substrate 2, the holes are formed. The high power laser beam is exima laser, YAG laser and the like. The holes formed in the substrate 2 may be through-holes or recesses.

The porous material 4 is produced to have a film like form with a film producing apparatus (not shown). In the film producing apparatus, a solution (hereafter dope), in which the polymer as a staff of the porous material is solved to a solvent, is cast on a substrate. The dope is thereafter gradually washed in water and dried after immersed in a bath containing solvent and nonsolvent of the polymer.

As the porous material, there are an organic type and an inorganic type, or may be also an organic/inorganic complex type.

The organic type is carbon porous material (activated carbon) and porous material of which a membrane filter is formed. Preferably, the porous material for forming the membrane filter is polymers which can be solved to a solvent for forming the porous material: cellulose derivatives (nitro cellulose, reproduced cellulose, cellulose acetate, acetylic cellulose, acetylic propylic cellulose, and the like), fatty group polyamides (nylon-6, nylon-66, nylon-4,10 and the like), polyolefins (polyethylene, polypropyrene, and the like), polymers including chlorine (polychloride vinyl, polychloride vinylidene and the like), fluoride resins (polyfluorovinylidene, polytetrafluoride and the like), polycarbonate, polysulfone, arginic acid and derivatives thereof (calcium arginate, arginic acid/polylisine polyion complex and the like), collagen and the like. Further copolymer of these polymers may be used.

The inorganic type is, preferably, metal (platinum, gold, iron, silver, nickel, aluminum and the like), oxide of metal (alumina, silica, titania, zeolite and the like), salt of metal (hydroxyapertite, calcium sulfide and the like), and their complexes.

In order to make the produced porous material 4 having the sheet like form stronger, unsolvable fiber-like materials may be mixed to the porous material 4. As the fiber-like material, there are cellulose, glass fiber, metallic fiber and the like, which hardly are solved to the solvent.

Further, the porous material may contain the following fiber material, such as cellulose derivatives, fatty acid polyamides and the like.

Figure 4:
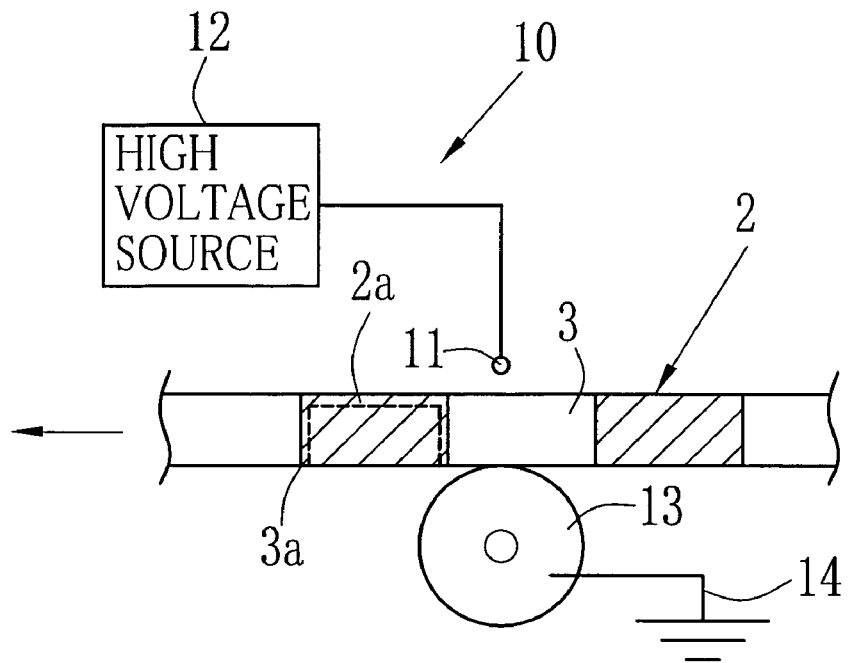
FIG. 4 is a diagrammatic sectional view illustrating the situation of processing a surface of the substrate.

In FIG. 4, the substrate 2 which is formed of a plastic material is continuously fed by a feeding device (not shown) for processing a surface of the substrate 2 in a corona discharging method. Above the surface of the substrate 2, a corona discharging device 10 is provided. The corona discharging device 10 includes an electrode 11, a high voltage source 12 and a roller 13. The roller 13 is grounded with a bar 14. When the discharge from the electrode 11 to the substrate 2 is made, then oxygen plasma generates in atmosphere containing oxygen. The oxygen plasma causes to introduce in the surface of the substrate 2 the polar groups, for example, carbonyl group, carboxylic group and the like. Thus the processed surfaces 2a, 3a are formed.

Figure 5:
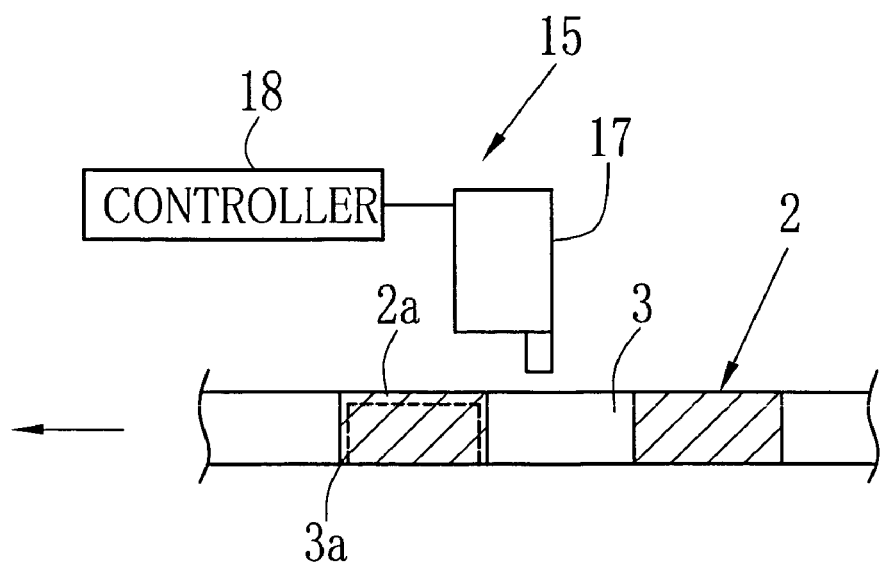
FIG. 5 is a diagrammatic sectional view illustrating another embodiment of processing the surface of the substrate.

In FIG. 5, a plasma discharging device 15 is provided above the substrate 2 which is continuously fed, for processing the surface in a plasma discharging method. The plasma discharging device 15 includes a head 17 and a controller 18. In the controller 18, a pump (not shown) is provided to supply the air to the head 17. In the head 17, a high voltage source and an electrode (not shown) are provided to change the air to the oxygen plasma. The oxygen plasma is applied to the substrate 2 by the head 17. When the substrate 2 is formed of metal, the oxygen plasma causes to form a processed surface on the substrate 2, which is a layer of the metal oxide. Further, when the substrate 2 is formed of plastic, the oxygen plasma causes to form the processed surface 2a, 3a on the substrate 2, in which the polar groups, for example, carbonyl group, carboxylic group and the like, are introduced.

In FIGS. 4 and 5, the surface of the substrate 2 is processed at a predetermined batch size in the corona discharging method or the plasma discharging method. Note that the structure of either the corona discharging device or the plasma discharging device is not restricted in FIGS. 4 and 5. Further, another plasma discharging device may be provided in another side of the substrate 2.

Figure 6:
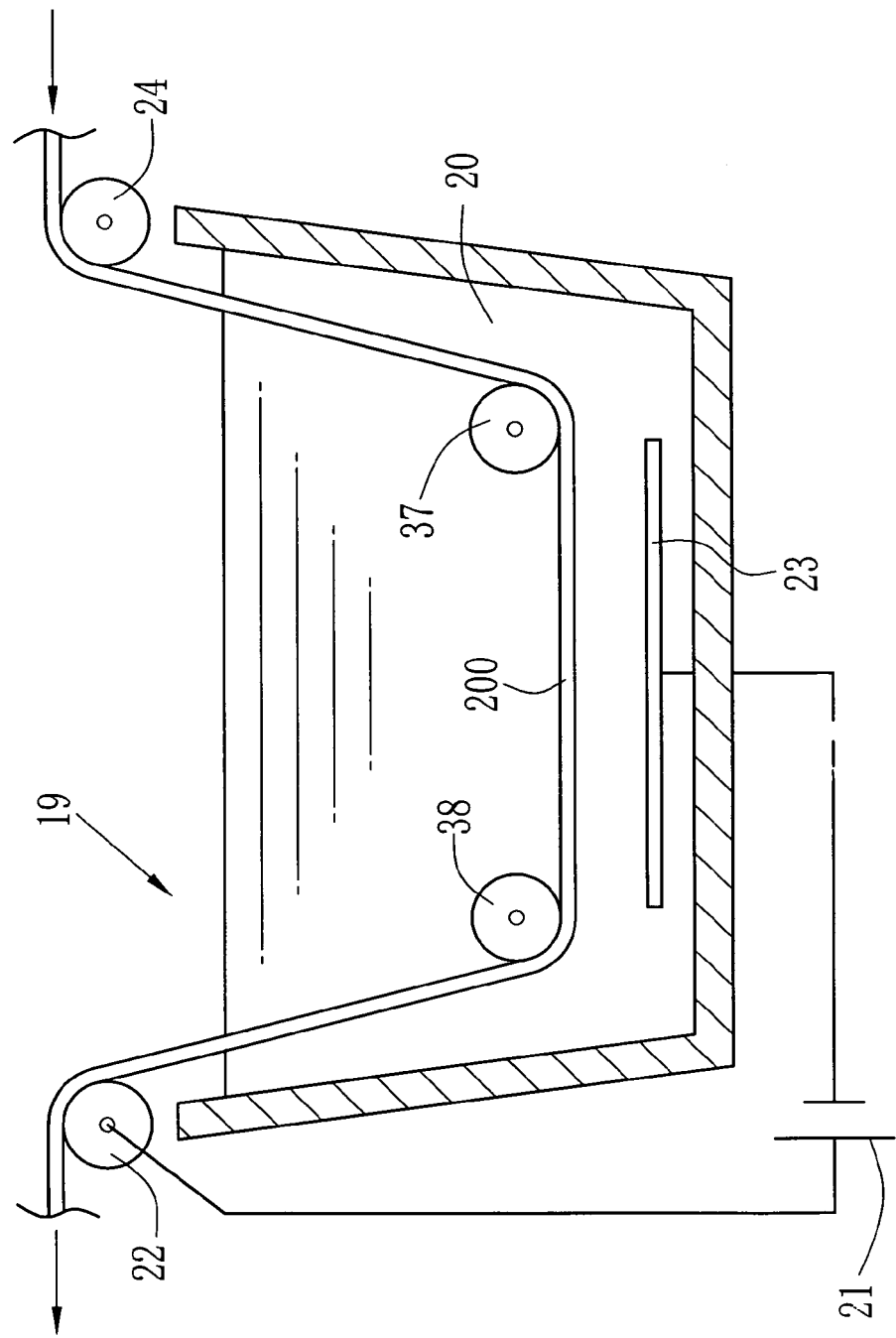
FIG. 6 is a diagrammatic sectional view illustrating the third embodiment of processing the surface of the substrate.

In FIG. 6, the surface of the continuous substrate 200 for producing the substrate 2 is processed in an oxidization bath 19 in an anodic oxidization method. In this case, the continuous substrate 200 has a conductivity, and is usually metal. Although the continuous substrate 200 is formed of aluminum in this embodiment, the present invention is not restricted in it. The oxidization bath 19 contains an electrolytic solution 20. Note that the electrolytic solution 20 is preferably 10% of an aqueous solution of sulfuric acid. However, the electrolytic solution 20 is not restricted in it, and may be phosphoric acid or oxalic acid, for example. A positive electrode of a electric power 21 is connected to a conductive roller 22, and a negative electrode is connected to an electrode 23. The electrode 23 is formed of metal, preferably platinum. When the electric power 21 supplies the straight flow between the conductive roller 22 and the electrode 23, then a chemical reaction represented in a following formula (1) is made on the continuous substrate 200 which is continuously fed in the electrolytic solution 20, such that the processed surface may be formed.

$$2Al + 3H_2O \rightarrow Al_2O_3 + 6H^+ + 6e^- \tag{1}$$

After cutting the continuous substrate 200 into the substrate 200, the surface processing processed in a batch method (the corona discharging method or the plasma discharging method, or the like) may be carried out. Further, the methods illustrated in FIGS. 4 and 5 may be applied for the continuous substrate 200 of FIG. 6.

Figure 7A:
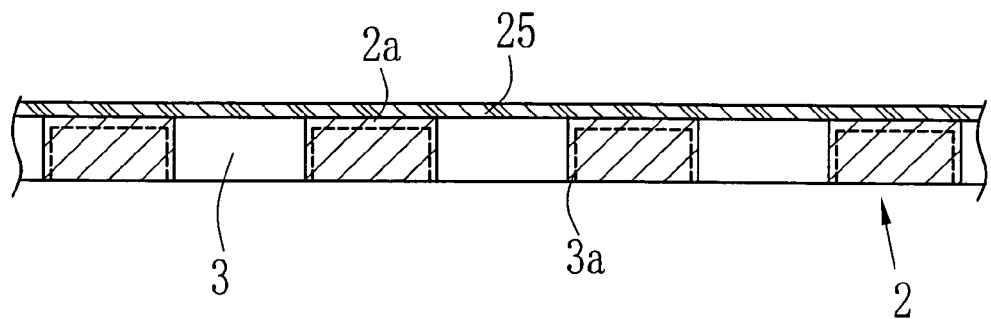
FIG. 7A is a sectional view illustrating a situation in which an adhesive agent is applied on the substrate.

After processing the surface of the substrate 2, as shown in FIG. 7A, an adhesive agent 25 is applied on the substrate 2 in method of dip coating, air knife coating, blade coating, bar coating and the like. The bar coating is especially preferable to apply the adhesive agent 25 uniformly. However, the method thereof is not restricted in it.

The adhesive agent 25 is preferably styrene butadiene rubber or acrylonitrile butadiene rubber. In this case, each material may have a glass transition temperature from −20 to 50° C. However, the kinds of the materials of the adhesive agent 25 are not restricted in them.

Figure 7B:
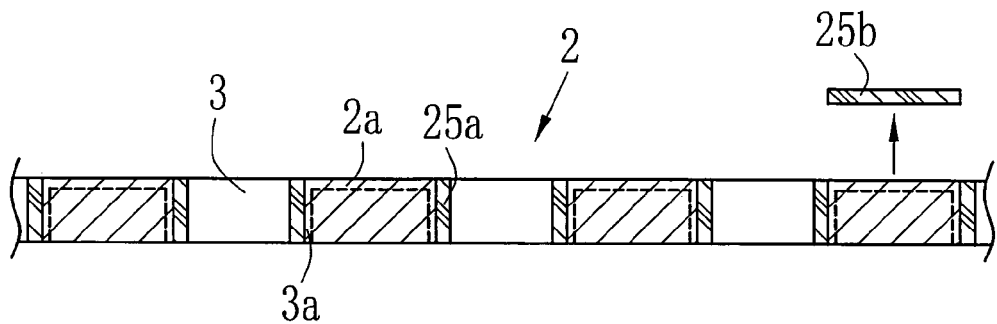
FIG. 7B is a sectional view of the case in a situation of removing the adhesive agent adhering to the substrate.

When the adhesive agent 25 is exposed as shown in FIG. 7A, dusts easily adhere thereto. Further, when the plural substrates 2 are piled up, or when the continuous substrate is rolled up, the surface of the substrate 2 adheres to the adhesive agent 25. Accordingly, the calcinations of the adhesive agent 25 are carried out at a temperature from 50 to 150° C. for 1-10 minutes. Thereby, as shown in FIG. 7B, walls of the holes 3 are coated with the adhesive agent 25. An excess adhesive agent 25b remaining on the substrate 2 may be scratched away, blown away, sucked away, or wiped out with a cloth during carrying out the calcinations. Thereafter the adhesive agent 25 is solidified and forms adhesive layer 25a on walls of the holes 3.

A large amount of the adhesive agent 25 often intrudes in the holes 3, or a membrane of the adhesive agent 25 is often formed so as to close the holes 3. In this case, it becomes harder to charge the porous material 4 in the holes 3, or the excess adhesive agent intrudes into small holes of the porous material. Accordingly, it is preferable that the excess adhesive agent in the holes 3 is removed.

Figure 7C:
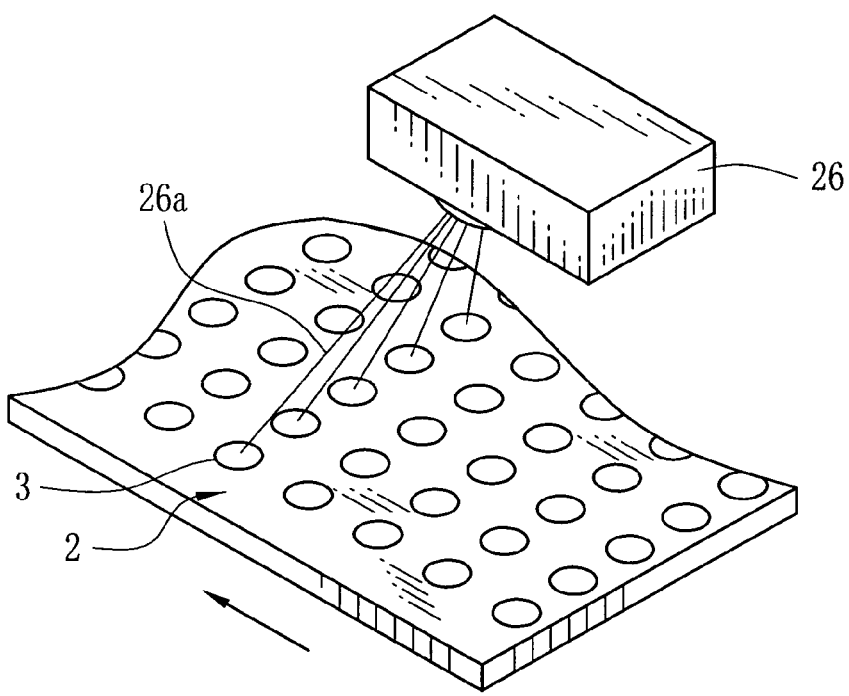
FIG. 7C is a perspective view of the substrate, illustrating a situation of removing an excess adhesive agent in the holes.

The removing of the excess adhesive agent in the holes 3 is more effectively made when a laser ablation device 26 is used after, before or at the same time of removing the excess adhesive layer 25c, as shown in FIG. 7C. In this case, the substrate 2 is fed in the feeding direction, and the laser ablation device 26 is disposed above the surface of the substrate 2. The laser ablation device 26 scans a laser beam 26a in a scanning direction perpendicular to the feeding direction on the substrate 2. Thereby the laser abrasion of the excess adhesive agent in the holes 3 is made. Thus the excess adhesive agent in the holes 3 is removed.

Further, there are other methods for removing the excess adhesive agent in the holes 3, such as a punching method using pins, a temperature adjusting method and the like. In the temperature adjusting method, the excess adhesive agent closing the holes 3 is melted to loss.

In the above embodiment, the processing of the surface is made in order to form the adhesive layer 25c on the wall of each hole 3 more stably. However, the processing may be omitted when adhesive layer 25a hardly peels from the wall of the holes 3.

Figure 8A:
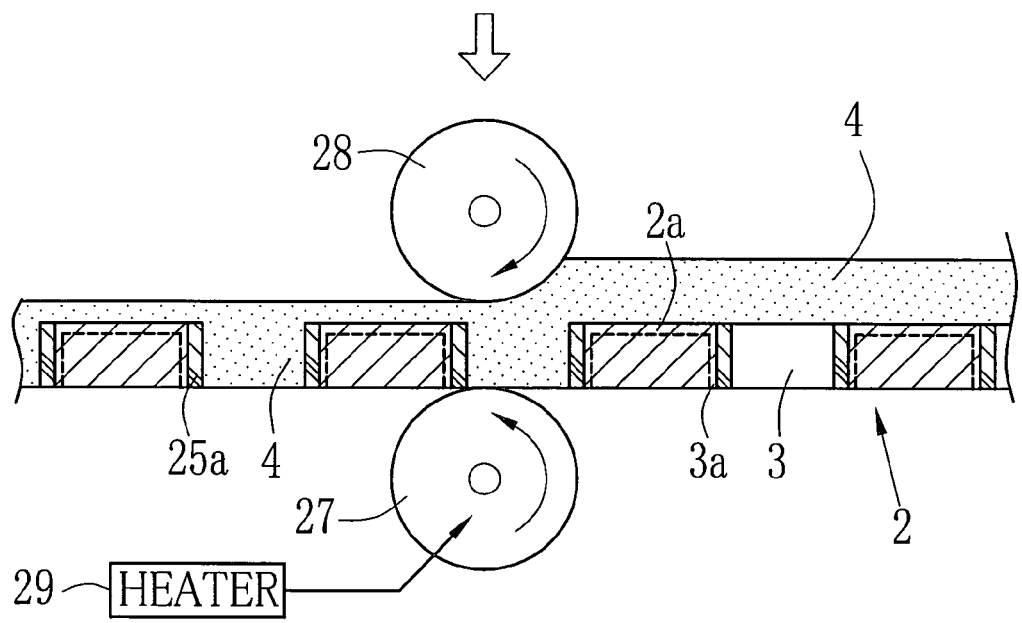
FIG. 8A is a diagrammatic sectional view illustrating a situation of charging holes of the substrate with a porous material.

In FIG. 8A, a press roller 28 which is connected to a heater 29 presses the porous material 4 to the substrate 2 supported by a backup roller 27. Thereby the porous material 4 is charged in the holes 3. In order to produce the porous material 4, a dope is applied on a support, and thereafter gradually washed in water and dried in air after immersed in a bath containing solvent of the polymer. After drying, the dope is peeled from the support to obtain the porous material 4. It is preferable that the main component of the porous material 4 is polyamide, such as nylon-6, nylon-66 and the like.

Figure 8B:
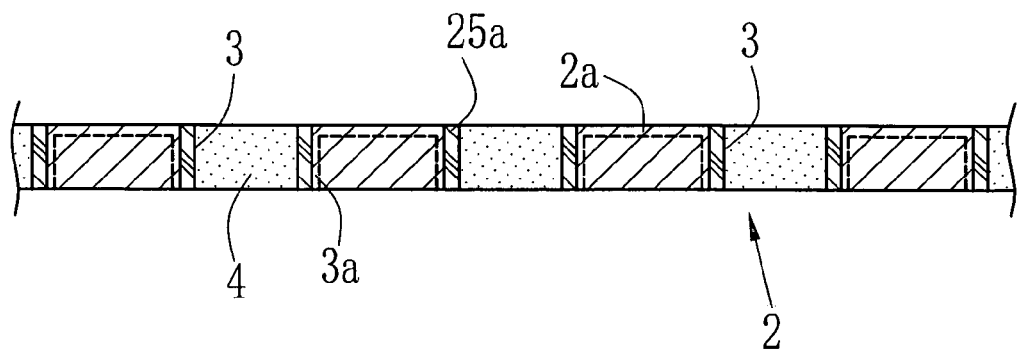
FIG. 8B is a sectional view of the biochemical analysis unit.

There is the excess porous material 4 remaining on a surface of the substrate 2. Preferably, as shown in FIG. 8b, the excess porous material 4 is removed to expose the holes 3 on both sides of the substrate 2.

When the press roller 27 is heated, the adhesive layer 25a is softened to have an adhesive effect. Accordingly, the adhesive layer 25a fixes the porous material 4 in the holes 3. It is preferable that the temperature of the backup roller 27 is higher than the glass transition temperature, and lower than the melting points of all of the adhesive layer 25a, the substrate 2, and the porous material 4. When the temperature of backup roller 27 is lower than the glass transition temperature, the adhesive layer 25a is not effective. Further, when the temperature of the adhesive layer 25a is higher than the melting points of all of the adhesive layer 30, the substrate 2, and the porous material 4, then the substrate 2 and other members are easily deformed. Note that the heater 29 may be already known, and not only the backup roller 27 but also the press roller 28 may be heated.

Note that the method of pressing the porous material 4 is not restricted in the above embodiment. For example, the substrate 2 and the porous material 4 may be pressed by a press plate, while intermittently fed with the feeding device. Further, the substrate and the porous material may be continuous sheets. In this case, they are continuously fed by pressing with the press roller to effectively charge the porous material in the holes, and thereafter, cut into tips to become the biochemical analysis units 1.

Note that a percentage of void of the porous material 4 is 10-90%, and the average pore diameter of the holes is 0.1-50 µm.

In order to accelerate the penetrating of the specific binding substance into the porous material, the surface of the porous material is often processed to become hydrophilic. For example, when the substrate 2 is made of conductive material, such as metal, the substrate 2 is grounded. Further, when the substrate 2 is made of insulating material, such as plastics and the ceramics, the substrate 2 is disposed on the conductive material which is earthed. Then the electrodes supplied in high voltage of alternating current are confronted to the substrate 2.

In order that the absorption of the specific binding substances in the porous material may be accelerated, it is preferable that the porous material contains the surface-active agent. As the surface-active agents, there are anion types, cation types and fluoride types: for example, potassium dodecylbenzenesulfonate, saponin, potassium p-tert-octylphenoxyethoxyethylsulfonate, nonylphenoxy-polyethoxy-ethanol; fluoride type surface-active agents which are disclosed in Japanese Patent Laid-Open Publications No. S62-170950, S63-188135 and U.S. Pat. No. 5,380,644; and polyalkyreneoxide and anion type surface-active agents which are disclosed in Japanese Laid-Open publication No. H6-301140.

According to the porous material in the porous material, a contact angle of water is preferably less than 60°, especially less than 50°.

Preferably, the porous material in the spot region 5 is retracted from the surface of the substrate 2. Thereby, the spotting of the specific binding substances on the porous material is more easily carried out. And the specific binding substance flows onto neither the surface of the substrate 2 nor the other absorptive spot regions 5.

As the specific binding substance, polynucleotide and oligonucleotide are conventionally used to forming the micro array. For example, cDNA, a part of cDNA, polynucleotide (PCR products) prepared in PCR method (for example, EST and the like), and synthesized nucleotide. Note that artificial nucleotide, that is, peptide nucleic acids (PNA) and derivatives thereof in which the phosphodiester bond of DNA is transformed into the peptide bond. Further, the specific binding substances spotted in the absorptive regions of the above embodiment may bind with the substance derived from a living organism such as a hormone, tumor marker, enzyme, antibody, antigen, abzyme, other protein, a nucleic acid, cDNA, DNA, RNA, or the like, whose sequence, base length, composition and the like are known.

Further, as described in U.S. Pat. No. 5,807,522, the specific binding substances are spotted onto the absorptive regions in spotting method and ink jetting method. In the spotting method, the specific binding substances are applied to a pin to transmit to the porous material. In the ink jetting method, a liquid containing the specific binding substances is jetted onto the porous material.

Preferably, the specific binding substances are bound in heat or illumination of the ultra-violet ray with the substances derived from living organism that is labeled with the labeling substance. As the reactions, there are hybridization of cDNA, antigene-antibody reaction, receptor-ligand and the like.

The labeling substance contains at least one of a radioactive labeling substance, a fluorescent labeling substance and a chemiluminescent labeling substance.

Note that the present invention is not restricted in the above embodiments. Especially the continuous substrate 200 of FIG. 6 may be used in embodiments illustrated in FIGS. 7A-8C. Thereby the continuous substrate 200 may be continuously fed in the feeding direction.

Figure 9A:
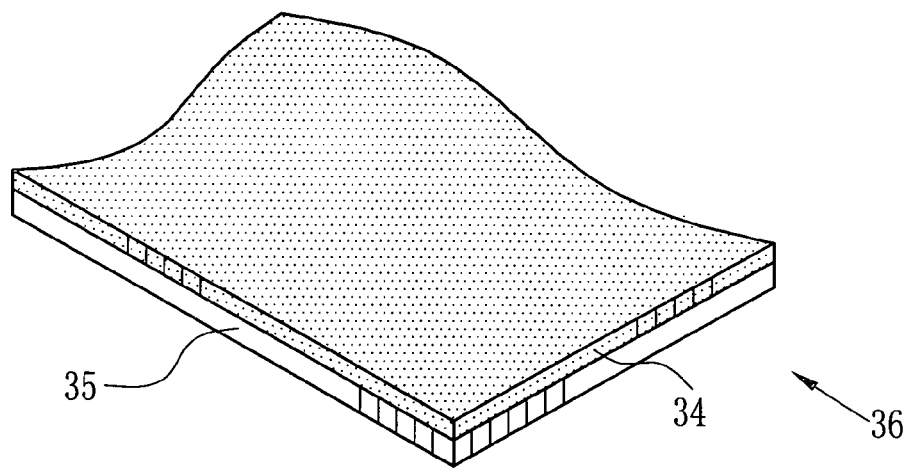
FIG. 9A is a perspective view of a stimulating phosphor sheet.

When the substances derived from living organism is labeled with the radioactive labeling substance, a stimulable phosphor sheet 36 in FIG. 9A is used for analysis. The stimulable phosphor sheet 36 includes a stimulable phosphor layer 34 made of a stimulable phosphor and a base 35.

Figure 9B:
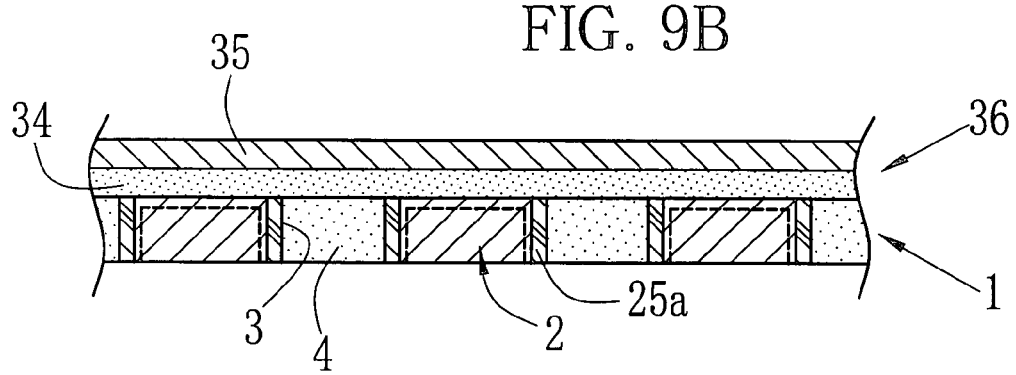
FIG. 9B is a sectional view of the stimulating phosphor sheet and the biochemical analysis unit which are overlapped.

As shown in FIG. 9B, the stimulable phosphor sheet 36 is overlapped on the biochemical analysis unit 1. Thereby the porous material 4 of the biochemical analysis unit 1 confront to the stimulable phosphor layer 34 of the stimulable phosphor sheet 37. Accordingly, the stimulable phosphor in the stimulable phosphor sheet 36 is exposed at a predetermined time to the radioactive ray emitted from the radioactive labeling substance. Thus energy of the radioactive ray is accumulated.

Thereafter the stimulable phosphor sheet 36 is set in an analyzing system (see, FIG. 10) and illuminated in a visible ray. Then the stimulable phosphor is exited and emits a light whose wavelength corresponds to the accumulated energy.

Figure 9C:
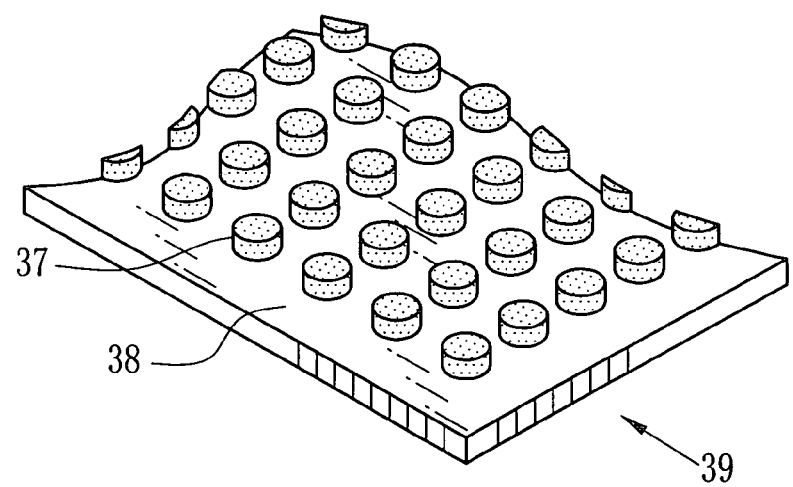
FIG. 9C is a perspective view of another embodiment of the stimulating phosphor sheet.

FIG. 9C is another embodiment of the stimulable phosphor sheet 39 which is used when the porous material in the biochemical analysis unit 1 is retracted from the surface thereof. The stimulable phosphor sheet 39 is constructed of the base 38 and detection protrusions 37 formed on the base 38. The detection protuberances 37 are formed in a matrix manner so as to correspond to the absorptive spot region of the biochemical analysis unit.

The stimulable phosphor is for example:
1) Japanese Patent Laid-Open Publication No. S55-12145 discloses alkaline earth material fluoride halide phosphors $(Ba_{1-x}M^{2+}_x)FX:yA$ (herein $M^{2+}$ is at least one of alkaline earth material Mg, Ca, Sr, Zn and Cd, X is at least one halogen of Cl, Br and I, and A is Eu, Tb, Ce, Tm, Dy, Pr, He, Nd, Yb and Er; $0 \leq x \leq 0.6$, $0 \leq y \leq 0.2$;
2) Japanese Patent Laid-Open Publication No. H2-276997 discloses alkaline earth material fluoride halide phosphors SrFX:Z (herein X is halogen, at least one of Cl, Br and I, and Z is Eu or Ce);
3) Japanese Patent Laid-Open Publication No. S59-56479 discloses europium activated complex halogen phosphors $BaFX.xNaX':aEu^{2+}$ (herein each X and X' is halogen, at least one of Cl, Br and I; $0 < x \leq 2$, $0 < a \leq 0.2$);
4) Japanese Patent Laid-Open Publication No. 58-69281 discloses cerium activated metal Oxyhalide, MOX:xCe (herein M is at least one of metals, Pr, Nd, Pm, Sm, Eu, Tb, Dy, Ho, Er, Tm, Yb and Bi, X is halogen, one or both of Br and I; $0 < x < 0.1$);
5) Japanese Laid-Open Publications No. 60-101179 and 60-90288 disclose cerium activated rear earth material oxyhalide phosphors LnOX:xCe (herein Ln is at least one of rear earth elements Y, La, Gd and Lu, X is at least one of halogens Cl, Br and I; $0 < x \leq 0.1$); and
6) Japanese Patent Laid-Open Publication No. S59-75200 discloses europium activated complex halide phosphor, $M^{(2)}FX.aM^{(1)}X'.bM'^{(2)}X''_2.cM^{(3)}X'''_3.xA:yEu^{2+}$ (herein $M^{(2)}$ is at least one of alkaline earth materials Li, Na, K, Rb and Cs, $M'^{(2)}$ is at least one of Be and Mg, $M^{(3)}$ is at least one of Al, Ga, In and Tl, A is at least one of oxides of metal, X is at least one of halogens Cl, Br and I, each X', X'' and X''' is one of halogens F, Cl, Br and I; $0 \leq a \leq 2$, $0 \leq b \leq 10^{-2}$, $0 \leq c \leq 10^{-2}$, $a+b+c \geq 10^{-2}$, $0 < x \leq 0.5$, and $0 < y \leq 0.2$).

The present invention is not restricted in the above embodiment. For example, unless the excess adhesive makes it hard to fill the porous material in the holes, the excess adhesive may not be removed from the surface of the substrate. Further, the processed surface is formed before applying the adhesive agent in the above embodiment. However, if the porous material is hardly removed from the substrate, then the processed surface may not be formed.

Figure 10:
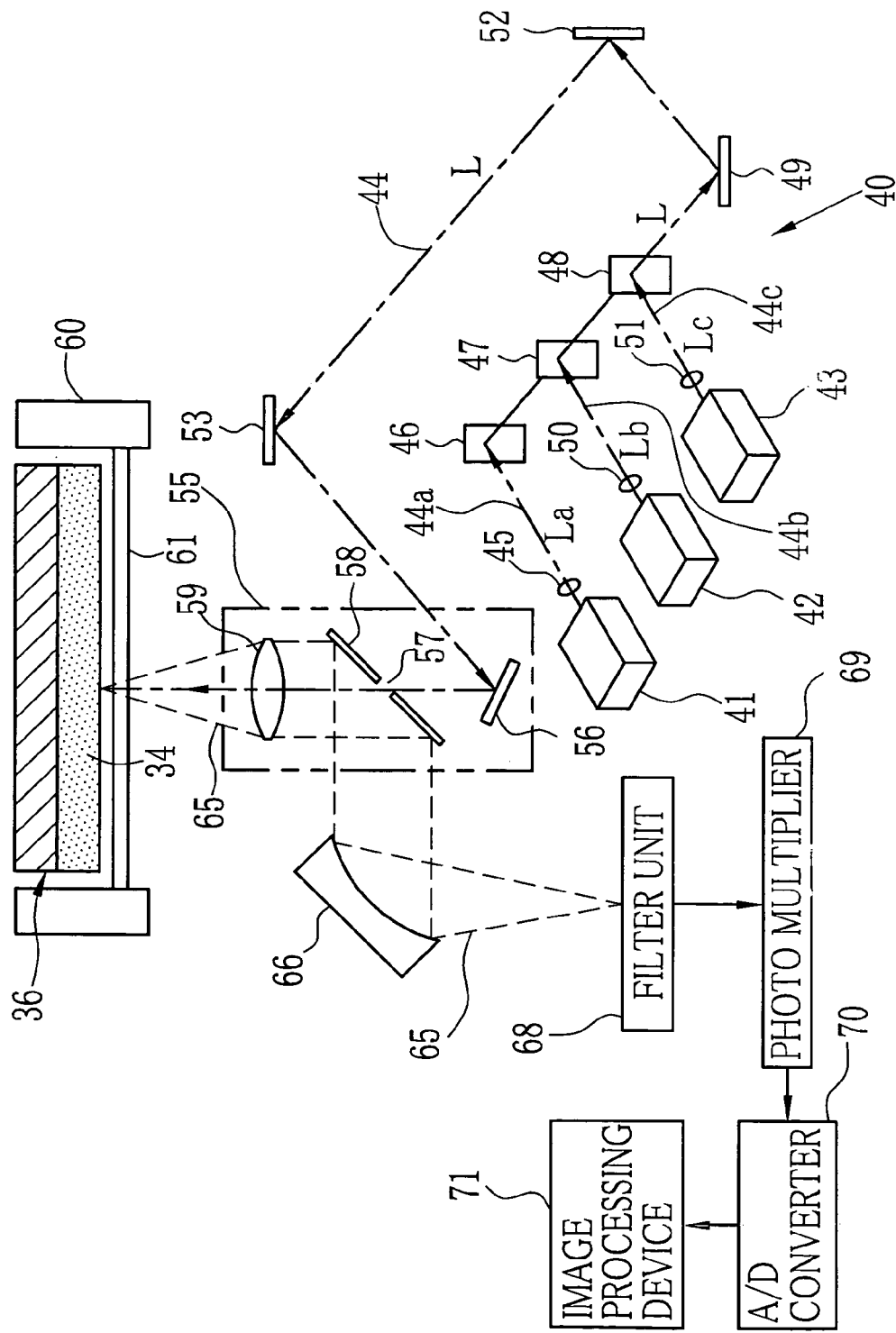
FIG. 10 is a schematic diagram of an analyzing system for carrying out a biochemical analysis by detecting an emission light from the stimulating phosphor sheet.

In FIG. 10, the data analysis system 40 is used for making the analysis of the substance derived from living organism. When the biochemical analysis is carried out, the substance derived from living organism that is labeled by a labeling substance is dropped in each absorptive spot region 5 to carry out the hybridization. Then, a stimulable phosphor sheet 36 is overlapped on the biochemical analysis unit 1 to expose the stimulable phosphor sheet 36 at a predetermined time. The exposed stimulable phosphor sheet 36 is set onto the glass plate 61 of a stage 40.

The data analysis system 40 includes first, second and third laser sources 41, 42, 43. The first laser source 41 is constructed of a semiconductor laser, and emits a laser beam 44a having wavelength of 640 nm. The second and third laser sources 42, 43 are constructed of second harmonic generation elements and emits a laser beam 44b having wavelength of 532 nm and a laser beam 44c having wavelength of 473 nm, respectively.

The scanner includes further first and second diachronic mirrors 47, 48 which selectively reflect the laser beams 44a, 44b, and 44c.

A laser beam 44a emitted from the first laser 21 is formed through a collimator lens 45 into a parallel beam, and is reflected by a mirror 46. A first diachronic mirror 47 and the second diachronic mirror 48 transmit the laser beam 44a. A laser beam 44b emitted from the second laser 42 is formed through a collimator lens 50 to be a parallel beam, and reflected by the first diachronic mirror 47. Then, the second diachronic mirror 48 transmits also the laser beam 44b. A laser beam 44c emitted from the third laser 43 passes through a collimator lens 51 to be a parallel beam, and reflected by the second diachronic mirror 48.

Thereafter, each of the laser beams 44a, 44b, 44c passes as an exiting beam 44 on an optical axis L in a light path and is reflected by mirror 49 and 52.

Downstream of the mirror 52, a perforated mirror 58 is disposed in the optical path. In a center of the perforated mirror 58 is formed a hole 57 through which the exiting beam 44 passes. Then the exiting beam 44 is reflected by a concave mirror 59 and enters into an optical head 55.

The optical head 55 includes a mirror 56 and an aspherical lens 59. After entering into the optical head 55, the exiting beam 44 is reflected by the mirror 56, and condensed by the aspherical lens 59 onto the stimulable phosphor sheet 36 on the glass plate 61. Thereby a fluorecent light 64 is discharged from the exposed spot region confronting to the absorptive spot region 5.

The fluorescent light 65 is formed by the aspherical lens 59 into a parallel light, and reflects on the perforated mirror 58. Then the fluorescent light 65 reflects on a concave mirror 66 and passes through a filter unit 68. Thereafter, the fluorescent light 65 is detected by a photo multiplier 69, which generates a detection signal. The detection signal is transformed into a detection data in an A/D converter 70. The detection data is sent to an image processing device 71. The image processing device 71 processes the detection data to display images on a display (not shown) in accordance with the detection data. Note that the optical head 55 is moved by a scanning mechanism (not shown) such that each of the exposed spot region 39 of the stimulable phosphor sheet 36 is entirely scanned.

EXAMPLE

Several types of the adhesive agents are used for adhering the porous material to the substrate. The example of the biochemical analysis unit is exampled the situations of peeling the porous material from the substrate. A SUS 340 having a thickness of 100 μm is cut to have a size 90 mm×70 mm, which is used as the substrate 2. The radius of the holes is 0.2 mm and an interval between the neighboring holes is 0.4 mm. The total number of the holes in the biochemical analysis unit is 100. In the biochemical analysis unit, 12 and 16 blocks are arranged in widthwise and lengthwise directions, respectively. Each block has a square shape, and a length of each side thereof is 4.5 mm. The nylon 66 whose thickness is 0.16 mm is used as the porous material 4. A percentage of void of the porous material 4 is 70%.

Three types of styrene butadiene rubber (SBR) of latex former are used as the adhesive agent. The glass transition temperature of the three type of the styrene butadiene rubber is 20, 40, and 60° C., respectively. Further, four types of acrylonitrile butadiene rubber (NBR) of latex former, whose glass transition temperature is −55, −30, −10, and 17° C. are also used as the adhesive agent.

[Forming of the Biochemical Analysis Unit]

The substrate is rinsed with pure water after ultra sonic cleaning with neutral detergent. In the oxidization bath 19 illustrated in FIG. 6, an electric current flows at 0.5 A in the electrolytic solution 20 for 5 minutes. Thereafter the substrate is rinsed with pure water. In the method of FIG. 7, the adhesive agent is applied to the substrate so as to have a thickness of 10 μm after dried. After applying the adhesive agent, the calcinations are made at 70° C. for five minutes. Further, the press roller is heated at 150° C., and the substrate and the porous material are pressed at a pressure 150 kgf/cm$^2$ to obtain a biochemical analysis unit.

The biochemical analysis unit is set in a buffer solution for DNA hybridization reaction at 65° C. for 18 hours, and then set in the boiling pure water for an hour. Thereafter, the biochemical analysis unit is left at −20° C. for 24 hours. These processes are made twice. Thereafter, the estimation of the biochemical analysis unit is made. Note that 100 ml of the buffer solution contains the following materials.

Sterilized pure water: 52 ml
20×SSC (3M NaCl, 0.3M Sodium citrate; produced by Nippon Gene Co., Ltd.): 30 ml
0.5M EDTA (Ethylenediaminetetraacetic acid; pH8.0)(2 ml)
50× Denhard's solution: 10 ml
10%-SDS solution (sodium dodecylsulfate solution): 5 ml
Deformed DNA of spermatozoa of sermon (100 μg/ml): 1 ml

[Estimation of Biochemical Analysis Unit]

in Estimation, the biochemical analysis unit is set in the buffer solution whose temperature is kept at 65° C. In this situation, it is examined whether the porous material is peeled from the substrate. When the porous material is not peeled, the estimation is "P". When the porous material is peeled, the estimation is "L". The results of the estimation are illustrated in Table 1.

TABLE 1

| Adhesive agent | Glass transition temperature | Estimation |
|---|---|---|
| SBR | 20° C. | P |
|  | 40° C. | P |
|  | 60° C. | L |
| NBR | −55° C. | L |
|  | −30° C. | L |
|  | −10° C. | P |
|  | 17° C. | P |

SBR: styrene butadiene rubber
NBR: acrylonitrile butadiene rubber

In Table 1, according to the biochemical analysis unit of the present invention, the porous material does not peel off from the wall of the hole of the substrate.

In the above embodiment, the laser ablation device removes the excess adhesive agent in the holes 3. However, the laser ablation device may be used for removing the adhesive agent 25b remaining on the substrate 2. Further, the laser ablation device can remove the adhesive agent 25b remaining on the substrate 2 and the excess adhesive agent in the holes 3 simultaneously.

Various changes and modifications are possible in the present invention and may be understood to be within the present invention.

What is claimed is:

1. A method for producing a biochemical analysis unit (1), comprising steps of:
   forming an adhesive layer (25a, 25b) on a wall of each hole formed in a base (2), said base (2) being sheet-like shaped;
   overlapping an absorptive material (4) with a surface of said base (2);
   pressing said absorptive material (4) to said base (2) with press member (27, 28) so as to charge part of said absorptive material (4) in said holes (3) and to adhere said absorptive material (4) to said wall of said hole (3) through said adhesive layer (25a, 25b).

2. A method as claimed in claim 1, wherein said press members (27, 28) are a press roller pair (27, 28), a first roller (27) of said press roller pair (27, 28) that contacts to said base is heated, and a temperature of said first roller (27) being higher than a glass transition temperature of said adhesive agent (25).

3. A method as claimed in claim 2, wherein said temperature of said first roller (27) is lower that all of said adhesive layer, said absorptive material and said base.

4. A method as claimed in claim 2, wherein said temperature of said first roller (27) is adjusted.

5. A method as claimed in claim 2, wherein said glass transition temperature is −20° C. to 50° C.

6. A method as claimed in claim 2, wherein said base (2) is formed of at least one of metal materials, ceramic materials and plastic materials.

7. A method as claimed in claim 2, a step for forming said adhesive layer (25a, 25b) comprising steps of:
   applying an adhesive agent (25) on said base (2); and
   carrying out calcinations of said adhesive agent (25) on said base (2).

8. A method as claimed in claim 7, further comprising a step of carrying out processing a surface of said base (2) in a corona discharging method, a corona discharging method, or a cathode oxidization method before the step of forming said adhesive layer (25a, 25b), in order to form said adhesive layer (25a, 25b) certainly.

9. A method as claimed in claim 7, wherein said adhesive agent (25) is styrene butadiene rubber or acrylonitrile butadiene rubber.

10. A method as claimed in claim 9, further comprising a step of blowing away, sucking away, or wiping out with a cloth an excess adhesive agent (25c) remaining on said surface of said base (2) before carrying out the calcinations.

11. A method as claimed in claim 10, further comprising a step of making laser ablation, punching, or heating after carrying out the calcinations, said laser ablation and said punching removing an excess adhesive agent in said holes (3), and said heating melting said excess adhesive agent in said holes (3).

* * * * *